(12) United States Patent
Miyoshi et al.

(10) Patent No.: US 9,409,168 B2
(45) Date of Patent: Aug. 9, 2016

(54) MICROFLUIDIC DEVICE

(71) Applicant: CANON KABUSHIKI KAISHA, Tokyo (JP)

(72) Inventors: Yuichi Miyoshi, Ushiku (JP); Daigo Kobayashi, Tokyo (JP); Hirotomo Taniguchi, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 104 days.

(21) Appl. No.: 13/962,074

(22) Filed: Aug. 8, 2013

(65) Prior Publication Data

US 2014/0044610 A1 Feb. 13, 2014

(30) Foreign Application Priority Data

Aug. 13, 2012 (JP) ................................. 2012-179384
Aug. 2, 2013 (JP) ................................. 2013-160964

(51) Int. Cl.
| | | |
|---|---|---|
| B32B 3/30 | (2006.01) | |
| B01L 3/00 | (2006.01) | |
| G01N 33/48 | (2006.01) | |
| B32B 3/02 | (2006.01) | |
| G01N 15/14 | (2006.01) | |
| G01N 33/50 | (2006.01) | |

(52) U.S. Cl.
CPC ..... *B01L 3/502707* (2013.01); *B01L 3/502715* (2013.01); *B01L 3/502723* (2013.01); *B01L 3/50273* (2013.01); *B01L 3/502746* (2013.01); *B01L 3/502761* (2013.01); *B01L 2200/027* (2013.01); *B01L 2200/0684* (2013.01); *B01L 2300/0816* (2013.01); *B01L 2300/1827* (2013.01); *B01L 2400/0406* (2013.01); *B01L 2400/0481* (2013.01); *B01L 2400/0487* (2013.01); *G01N 15/147* (2013.01); *G01N 15/1484* (2013.01); *G01N 33/5008* (2013.01)

(58) Field of Classification Search
CPC ................... B01L 3/502707; B01L 3/502715; B01L 3/502746; B01L 2400/0481; B01L 2200/027; B01L 2400/0487; B01L 2300/0816; B01L 2400/0406; B01L 2200/0684; B01L 3/502761; G01N 15/147

See application file for complete search history.

(56) References Cited

U.S. PATENT DOCUMENTS

| | | | |
|---|---|---|---|
| 2003/0026740 A1* | 2/2003 | Staats ................... | B01L 3/0268 422/503 |
| 2007/0200081 A1* | 8/2007 | Elizarov ............ | B01L 3/502707 251/331 |
| 2010/0186839 A1* | 7/2010 | Namkoong ....... | B01L 3/502738 137/825 |
| 2011/0008223 A1 | 1/2011 | Tsao et al. | |
| 2012/0058519 A1 | 3/2012 | Knight et al. | |
| 2012/0107912 A1* | 5/2012 | Hwang et al. ............... | 435/235.1 |
| 2012/0107925 A1* | 5/2012 | Li et al. .......................... | 435/325 |
| 2012/0118392 A1* | 5/2012 | Blankenstein et al. ........... | 137/1 |

* cited by examiner

*Primary Examiner* — Jennifer Wecker
(74) *Attorney, Agent, or Firm* — Fitzpatrick, Cella, Harper & Scinto

(57) ABSTRACT

The present invention provides a microfluidic device which is molded with a die and has a specimen inlet part. The microfluidic device has the specimen inlet part. The specimen inlet part has an inlet channel for introducing a specimen into the flow channel, wherein the inlet channel has a diameter which continuously and gradually increases as the inlet channel approaches the flow channel, or has a diameter which is constant in the vicinity of an inlet port and then continuously and gradually increases as the inlet channel approaches the flow channel.

9 Claims, 9 Drawing Sheets

MICROFLUIDIC DEVICE

BACKGROUND OF THE INVENTION

1. Field of the Invention

The present invention relates to a microfluidic device which has a specimen inlet part.

2. Description of the Related Art

In recent years, a technology is proposed which enables an analysis with a unit of several µL to nL, by forming a fine reaction field by using a lithographic process technology or a thick-film process technology. A technology using such a fine reaction field is referred to as µ-TAS (Micro Total Analysis System).

The µ-TAS technology is applied to: a region of a genetic test, a chromosomal test, a cytoscopy and the like; a biotechnology; a test of a trace amount of a substance in an environment; an investigation on a farming environment of an agricultural product and the like; a genetic test for an agricultural product; and the like. Great effects such as an automation, an increase of the speed, an increase of the accuracy, a reduction of the cost, a reduction of the period of time, and a reduction of the environmental impact can be obtained by the introduction of the µ-TAS technology.

In µ-TAS, in many cases, a flow channel with a micro size (micro flow-channel or micro channel) is used, which is formed on a substrate. Such a substrate is referred to as a chip, a microchip, a microfluidic device or the like.

One of subjects when a microfluidic device is used is how a specimen (sample) is introduced, and the subject is important particularly when the device is automated.

The first object of the present invention is to provide a microfluidic device which can introduce a specimen thereinto without causing a mixture of air bubbles. When the air bubbles are mixed, such a problem occurs that a fed liquid becomes turbulent and a flow channel is blocked.

The second object of the present invention is to provide a microfluidic device which can be manufactured with molding. A chip part, in particular, out of the whole micro flow-channel device is formed so as to be disposable in many cases, and accordingly, it is important to reduce a manufacturing cost of the chip. In order to reduce the cost, the microfluidic device is desirably manufactured with molding.

U.S. Patent Publication No. 2012-0058519 discloses a method of attaching a thin glass tube having a diameter of approximately 0.1 mm to a chip, which functions as an access tube, and introducing a specimen into the chip by a capillary phenomenon, as a method for introducing a specimen. If the capillary phenomenon is used, a sample can be introduced without the introduction of the air bubbles. However, labor is needed to attach the glass tube to the chip resulting in an increase in cost.

U.S. Patent Publication No. 2011-0008223 discloses another form of a specimen inlet part.

SUMMARY OF THE INVENTION

The present invention provides a microfluidic device which is molded with a die and has a specimen inlet part, wherein the specimen inlet part has an inlet channel for introducing a specimen into the flow channel, wherein the inlet channel has a diameter which continuously and gradually increases as the inlet channel approaches the flow channel, or has a diameter which is constant in the vicinity of an inlet port and then continuously and gradually increases as the inlet channel approaches the flow channel.

Further features of the present invention will become apparent from the following description of exemplary embodiments with reference to the attached drawings.

BRIEF DESCRIPTION OF THE DRAWINGS

FIG. 1A is a 3D view, FIG. 1B is a transmissive view, FIG. 1C is a cross-sectional view, and FIG. 1D is a cross-sectional view.

FIG. 2A illustrates a microfluidic device having a specimen inlet part, FIG. 2B illustrates a component which forms a hole shape, and FIG. 2C illustrates a component which forms the flow-channel shape.

FIG. 3A illustrates a device for the analysis and a view illustrating details of the device for the analysis, and FIG. 3B illustrates an enlarged view of a chip made from glass.

FIG. 4A is a view illustrating the first step in which the first specimen is guided to the microfluidic device having the specimen inlet part, FIG. 4B is a view illustrating the second step in which the first specimen is guided from the microfluidic device having the specimen inlet part to the chip made from glass, FIG. 4C is a view illustrating the third step in which the second specimen is guided to the microfluidic device having the specimen inlet part, FIG. 4D is a view illustrating the fourth step in which the second specimen is guided from the microfluidic device having the specimen inlet part to the chip made from glass, and FIG. 4E is a view illustrating the state in which several kinds of specimens have been guided to the device for the analysis.

FIG. 5A is a view illustrating the state in which the specimen inlet part is filled with the first specimen, FIG. 5B is a view illustrating a state in which a syringe that has inserted the second specimen into the specimen inlet part is arranged on an upper part of the specimen inlet part, FIG. 5C is a view illustrating a step in which the second specimen is added to the specimen inlet part dropwise from the syringe, and is guided into the specimen inlet part, and FIG. 5D is a view illustrating the state in which the specimen inlet part is filled with the second specimen.

FIG. 6A illustrates an example in which contamination does not easily occur, FIG. 6B illustrates an example in which the contamination easily occurs, and FIG. 6C illustrates an example in which the contamination does not easily occur.

FIG. 9A is a view illustrating that the cross section is a petal shape, and FIG. 9B is a view illustrating that the cross section is a petal shape.

FIG. 10A is a view illustrating a configuration where the droplet and the waste liquid mixes with each other, and FIG. 10B is a view illustrating a configuration where the droplet and the waste liquid does not mix with each other.

DESCRIPTION OF THE EMBODIMENTS

Preferred embodiments of the present invention will now be described in detail in accordance with the accompanying drawings.

The present invention provides a microfluidic device which is molded with a die and has a specimen inlet part, wherein the specimen inlet part has an inlet channel for introducing a specimen into the flow channel, wherein the inlet channel has a diameter which continuously and gradually increases as the inlet channel approaches the flow channel, or has a diameter which is constant in the vicinity of an inlet port and then continuously and gradually increases as the inlet channel approaches the flow channel.

The present invention also provides the microfluidic device which has the specimen inlet channel with a diameter of 0.5 mm or not more than 0.5 mm at the inlet port.

The present invention also provides the microfluidic device, wherein the specimen inlet part has an outer diameter thereof which continuously and gradually increases from an upper face thereof to a bottom face thereof.

The present invention also provides the microfluidic device, wherein the specimen inlet part has an outer wall with a thickness of 0.4 mm or not more than 0.4 mm at the inlet port.

The present invention also provides the microfluidic device, wherein the specimen inlet part has a height of 2 mm or not less than 2 mm.

The present invention further provides any one of the microfluidic devices, wherein the specimen inlet channel has a bump in an inner part thereof and on the bottom face of the specimen inlet part.

The microfluidic device is a substrate having a micro flow-channel, and includes a DNA chip, a Lab on a Chip, a microarray and a protein chip, for instance.

The molding is a working method for resin, plastic, metal and the like, and refers to a method of filling a die with the resin, plastic, metal or the like and molding the material thereof. A base material of the microfluidic device of the present invention is not limited in particular, as long as the base material can be molded with the die, and the base materials to be used there include resins of COP (cycloolefin polymer), PMMA (polymethyl methacrylate), PC (polycarbonate), MS (methyl methacrylate styrene copolymer) and PS (polystyrene).

Figure 2A:
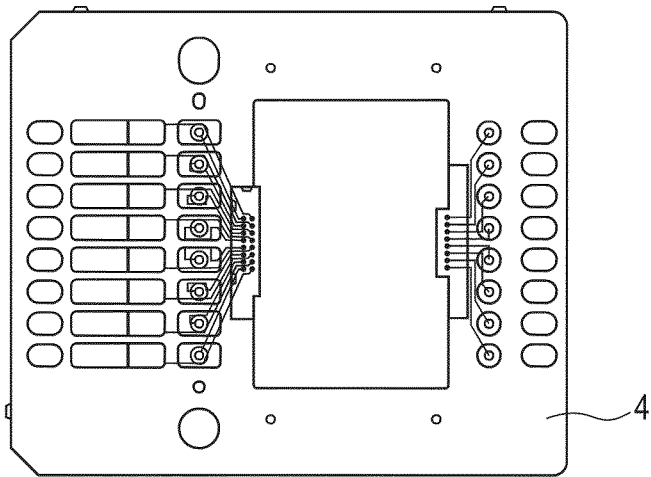
FIGS. 2A, 2B and 2C illustrate a microfluidic device having a specimen inlet part.
Figure 2B:
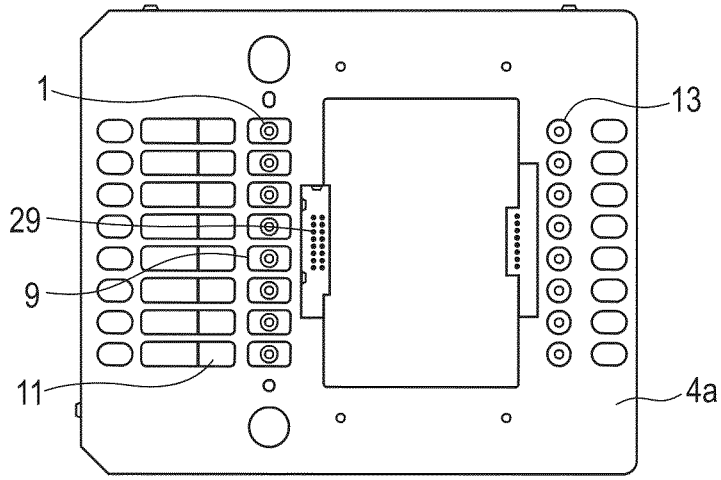
Figure 2C:
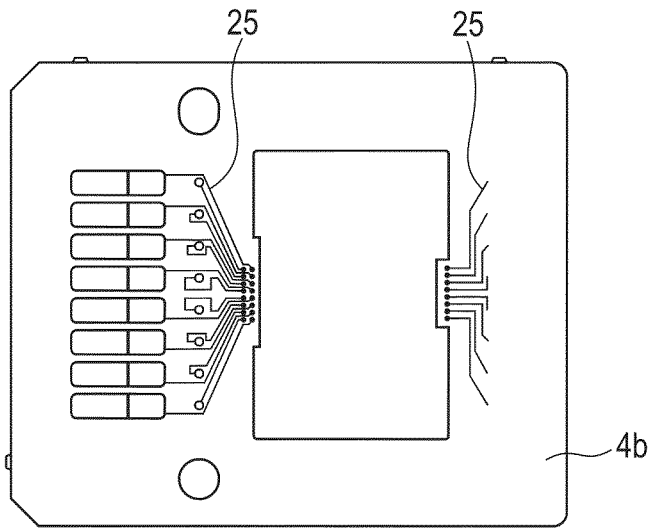

For information, the microfluidic device may not be necessarily molded with one die, but components may be bonded to each other after the molding to complete the microfluidic device. For instance, the microfluidic device in FIG. 2A is manufactured by a process of molding respective components which are illustrated in FIG. 2B and FIG. 2C, and then bonding the components to each other.

The specimen inlet part refers to a portion for introducing a liquid such as a specimen into the flow channel therethrough. The specimen inlet part has the inlet channel which leads to the flow channel from the inlet port, and the specimen or the like is sent into the flow channel through the inlet channel.

In the specimen inlet part in the present invention, the liquid introduced thereinto keeps its shape even to the inlet port of the specimen inlet channel or to the vicinity of the inlet port, due to the surface tension. Accordingly, the present invention has such a feature that when the specimen is intermittently introduced into the inlet port, air bubbles do not enter a gap between the specimen and the inlet port.

In the present invention, a meaning of such a phrase that the diameter of the inlet channel continuously and gradually increases includes that the diameter gradually increases linearly at a constant rate, but the diameter does not necessarily need to gradually increase linearly at the constant rate.

In addition, a cross section of the inlet channel does not necessarily need to be a circle, but may be an elliptical shape, a polygonal shape or another shape. The diameter refers to a diameter when the cross section is a circle, and refers to a value obtained by doubling an average of distance from a central position, when the cross section has another shape.

When the inlet channel has a portion with a constant diameter in the vicinity of the inlet port, the portion is referred to as a mouth part in the present specification.

Figure 3A:
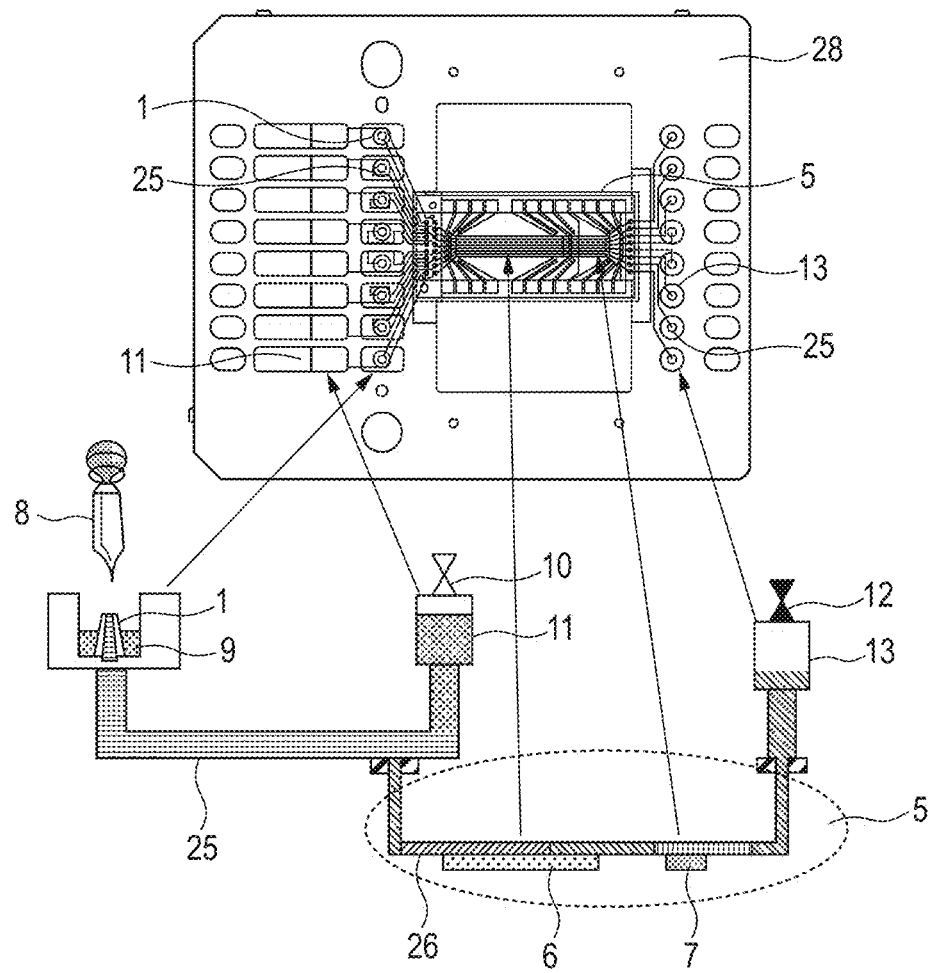
FIGS. 3A and 3B illustrate a device for the analysis.
Figure 3B:
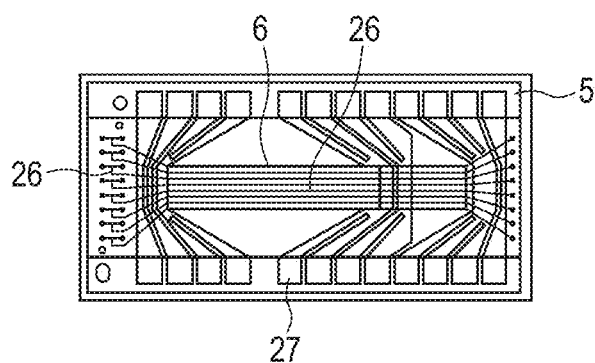

The microfluidic device of the present invention can be used for sending a liquid to a second micro flow-channel. The second micro flow-channel may exist in a form of the second microfluidic device, or may also exist in a form other than the chip. The following FIGS. 3A and 3B illustrate an example in which the second micro flow-channel exists in a microfluidic device 5 made from glass, which is the second microfluidic device. The second microfluidic device may be molded with a die or may not be molded with a die. The chip made from glass is superior in heat resistance, and accordingly is desirably used when the introduced specimen is amplified by PCR.

In addition, a second embodiment of the present invention provides a microfluidic device which further has a bump in an inner part of the specimen inlet channel. The bump refers to a substance for substantially reducing a volume in the specimen inlet channel, and its material, its shape and its position in the inner part of the specimen inlet channel may not be considered.

In addition, a third embodiment of the present invention provides a method for manufacturing a microfluidic device, which includes: preparing a die which has a shape for transferring an outer wall of a specimen inlet part formed therein; preparing a die which has a projection part having a shape for transferring an inner wall of the specimen inlet part formed therein; combining the dies to form a cavity therebetween; filling the cavity with a resin to form a component which forms the specimen inlet part; and manufacturing the microfluidic device.

In this method, it is possible to form a component which forms the flow channel by a die having a shape for transferring the flow channel therein, and bond the component with the component which forms the specimen inlet part.

In addition, the die which has the projection part having the shape for transferring the inner wall of the specimen inlet part formed therein may further have a shape for transferring a flow channel formed therein, and the die which has the shape for transferring the outer wall of the specimen inlet part formed therein may further have a shape for transferring an outer wall of a liquid storage part and a shape for transferring a bottom face of the liquid storage part formed therein.

The present invention will be described more in detail below with reference to the drawings.

[Exemplary Embodiment 1]

Study on Shape of Inlet Channel of Specimen Inlet Part

It is difficult to mold the specimen inlet part which has an inlet channel having a shape with a constant diameter (column, for instance) with a die, and accordingly the specimen inlet part having a shape with a constant diameter cannot be molded with a die. Accordingly, the specimen inlet part of the present invention has such a shape that the diameter of the inlet channel continuously and gradually increases as the inlet channel approaches the flow channel, or is constant in the vicinity of an inlet port and then continuously and gradually increases as the inlet channel approaches the flow channel. In other words, in a cross-sectional shape that has been formed when the inlet channel has been cut in an optional plane containing a central axis of the inlet channel, the specimen inlet part has a shape in which a distance between inner walls in a direction perpendicular to the central axis continuously and gradually increases as the inlet channel approaches the flow channel. Incidentally, the distance between the inner walls in the direction perpendicular to the central axis is referred to as the diameter of the inlet channel, in the present specification.

Figure 1A:
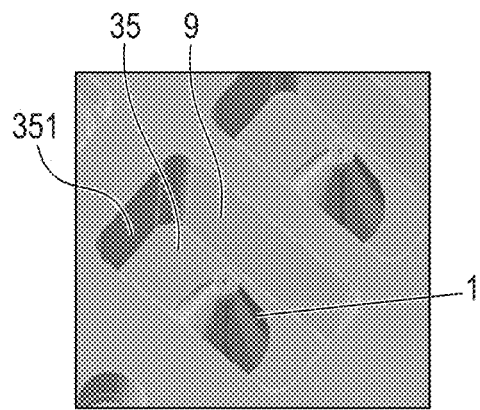
FIGS. 1A, 1B, 1C and 1D illustrate a specimen inlet part.
Figure 1B:
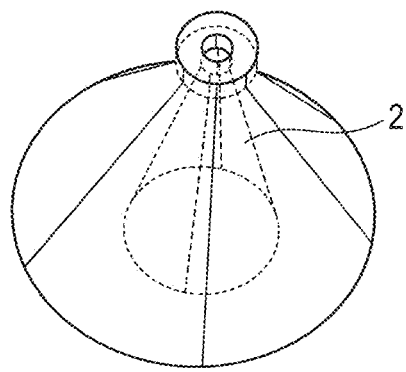
Figure 1C:
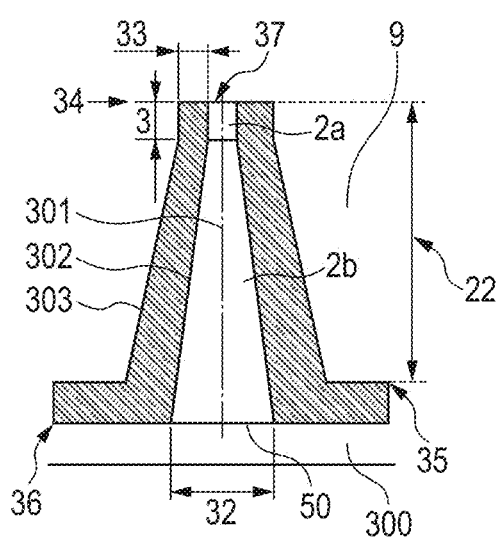
Figure 1D:
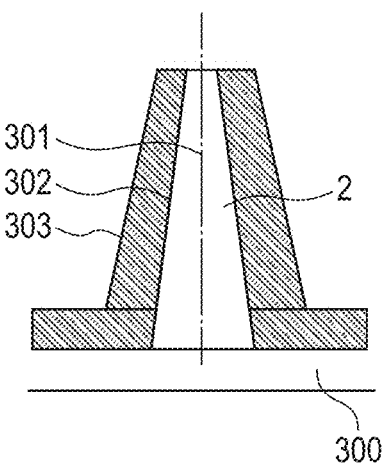

FIGS. 1A, 1B, 1C and 1D illustrate the specimen inlet part 1 of a microfluidic device of the present invention. FIG. 1A is a 3D view of an appearance of the specimen inlet part 1. FIG. 1B is a transmissive view of the specimen inlet part 1, and illustrates that the specimen inlet part 1 has an inlet channel 2 in its inner part. FIGS. 1C and 1D illustrate examples of a cross-sectional shape including the central axis of the flow channel of the specimen inlet part 1.

FIGS. 1A, 1B and 1C illustrate an example of the inlet channel which has a mouth part. The FIGS. 1A, 1B, and 1C illustrate the specimen inlet part having the inlet channel in which the distance (diameter) between inner walls in a direction perpendicular to the central axis is constant in the vicinity 2a of the inlet port, and then linearly and gradually increases as the inlet channel approaches the flow channel (in the inlet channel 2b), in the cross-sectional shape that has been formed when the inlet channel has been cut in an optional plane containing the central axis of the inlet channel. A distance (diameter) 32 between the inner walls at a junction of the inlet channel with the flow channel 300 is shown. FIG. 1D illustrates an example of the inlet channel having the diameter which linearly and gradually increases as the inlet channel approaches the flow channel.

When the inlet channel of the specimen inlet part has the diameter which gradually increases as the inlet channel approaches the flow channel, specifically, when the inner shape of the inlet channel is a frustum, or when the inlet channel has the mouth part and includes the frustum and the mouth part (example: combination of truncated cone and column), the die is easily produced, and accordingly can be produced at a low cost. Preferably the mouth part has a height 3 of 0.5 mm or not more than 0.5 mm. The reason is that it becomes difficult to produce the die if the height exceeds 0.5 mm.

The specimen inlet part increases its strength by having the mouth part provided therein, which may be more advantageous when the specimen inlet part is molded with a die.

The inlet channel does not need to have a cross section (which has been formed when inlet channel has been cut in plane in direction perpendicular to central axis) of a circular shape, but may have an elliptical shape, a polygonal shape or another shape. The cross section can be a circle, a polygonal shape having five angles or more, or an elliptical shape. But if the cross section is a triangle or a quadrangle, having an acute angle at portions of the angles, the specimen liquid easily remains at the angle portions of the bottom face and the side face due to surface tension.

The specimen inlet part may have a liquid reservoir 9 in the outer periphery thereof. The distance (height of liquid reservoir) 22 from the bottom part 35 of the liquid reservoir to a face 34 in the direction perpendicular to the central axis of the inlet port 37 of the specimen inlet part can be 2 mm or more. When the thickness 33 of the wall of the inlet port is excessively large, discharge efficiency decreases, and accordingly the thickness of the wall of the inlet port is desirably 0.4 m or not more than 0.4 m.

As for the outer wall 303 of the specimen inlet part, in a cross-sectional shape that has been formed when the inlet channel has been cut in an optional plane containing the central axis of the inlet channel, a distance between the outer walls in the direction perpendicular to the central axis linearly and gradually increases as the inlet channel approaches the bottom face 35 of the liquid reservoir. In the present specification, the distance between the outer walls in the direction perpendicular to the central axis is referred to as the outer diameter.

[Exemplary Embodiment 2]

Example of Manufacture and Use of Microfluidic Device of the Present Invention

FIGS. 2A, 2B and 2C illustrate the examples of the manufacture of the microfluidic device 4. FIG. 2A is a view illustrating the microfluidic device 4. FIG. 2B is a view illustrating one component of the microfluidic device 4. FIG. 2C illustrates another component of the microfluidic device 4. A component 4a which forms the specimen inlet part, a component 4b which forms the flow-channel shape, the flow channels 25 and holes 29 which connect the microfluidic device 4 with a chip made from glass are shown.

Specifically, the microfluidic device 4 is formed of two component bodies (4a/4b), and the components are bonded to each other with thermo compression bonding or adhesive bonding to form the microfluidic device 4 having the specimen inlet part.

Figure 11A:
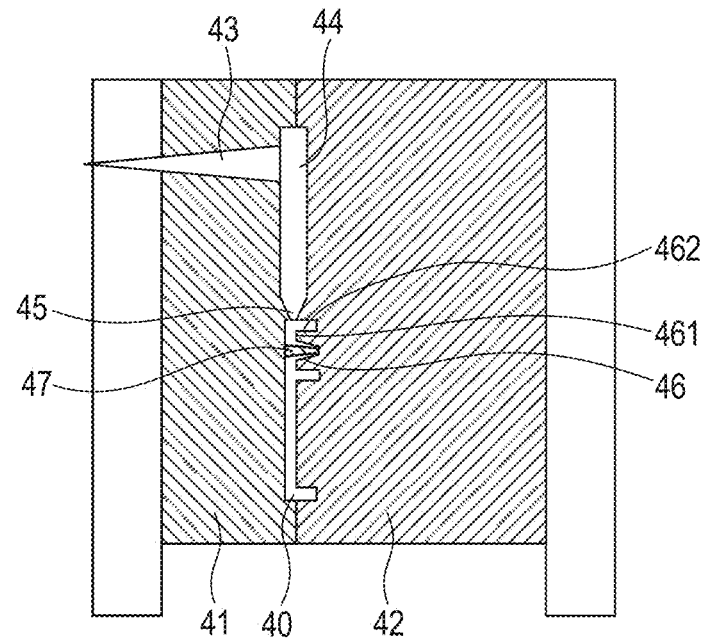
FIG. 11A is a view illustrating a method for manufacturing the component 4a which forms the specimen inlet part.
Figure 11B:
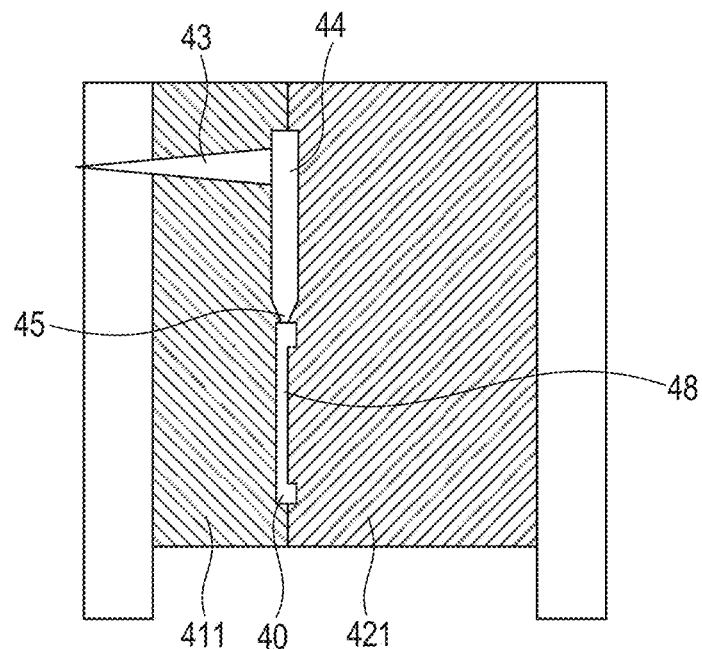
FIG. 11B is a view illustrating a method for manufacturing the component 4b which forms the flow-channel shape.

FIG. 11A is a view illustrating a method for manufacturing the component 4a which forms the specimen inlet part. FIG. 11B is a view illustrating a method for manufacturing the component 4b which forms the flow-channel shape.

FIG. 11A illustrates a die for molding the component 4a which forms the specimen inlet part. The component 4a which forms the specimen inlet part includes the inner wall 302 of the inlet channel of the specimen inlet part, the outer wall 303 of the specimen inlet part, the bottom face 35 of the liquid reservoir 9, and the outer wall 351 of the liquid reservoir, which are illustrated in FIG. 1A. Firstly, a projection part 47 is formed in a first die 41, which has a shape for transferring the inner wall 302 of the inlet channel of the specimen inlet part.

In addition, the shapes are formed in a second die 42, which are a shape 46 for transferring the outer wall 303 of the specimen inlet part, a shape 461 for transferring the bottom face 35 of the liquid reservoir 9, and a shape 462 for transferring the outer wall 351 of the liquid reservoir. Then, the component 4a which forms the specimen inlet part is manufactured by a process of injecting a resin into a cavity which is formed by combining the first die 42 with the second die 41, through a sprue 43, a runner 44 and a gate 45, and cooling and solidifying the injected resin.

FIG. 11B illustrates a die for molding the component 4b which forms the flow channel. The component 4b which forms the flow channel has the flow channel 300 which is illustrated in FIG. 1C. A shape 48 for transferring the flow channel is formed, for instance, in a fourth die 421. Then, the component 4b which forms the flow channel is manufactured by a process of filling the cavity which is formed by combining a third die 411 with the fourth die 421, with a resin through a sprue 43, a runner 44 and a gate 45, and cooling and solidifying the filled resin.

Thus manufactured component 4a which forms the specimen inlet part and component 4b which forms the flow channel are bonded to each other with thermo compression bonding or adhesive bonding, and thereby the microfluidic device 4 having the specimen inlet part is manufactured.

The shape 48 for transferring the flow channel 300 can be formed also in the first die 41 together with the projection shape 47 having the shape for transferring the inner wall 302 of the inlet channel of the specimen inlet part. Then, the shapes are formed in the second die 42, which are the shape 46 for transferring the outer wall 303 of the specimen inlet part, the shape 461 for transferring the bottom face 35 of the liquid storage part 9, and the shape 462 for transferring the outer wall 351 of the liquid reservoir. Then, the component having the specimen inlet part and the flow-channel portion formed therein is manufactured by a process of injecting a resin into a cavity which is formed by combining the first die 41 with the second die 42, through the sprue 43, the runner 44 and the gate 45, and cooling and solidifying the injected resin. Then, the microfluidic device 4 having the specimen inlet part can be produced by a process of bonding the manufactured component with a flat plate.

FIGS. 3A and 3B illustrate a device 28 for analysis, in which the microfluidic device having the specimen inlet part is bonded with the chip that is made from glass and is the second micro flow-channel.

In the figures, the specimen inlet part 1, the microfluidic device 4 having the specimen inlet part, the chip 5 made from glass, a syringe 8, the liquid reservoir 9, micropumps 10 and 12, specimen discharge ports 11 and 13, a heater 6 for heating, a portion 7 for measuring quantity of fluorescence, flow channels 25 of the microfluidic device having the specimen inlet part 1, flow channels 26 of the chip made from glass and wiring 27 for the heater are shown.

The specimen is introduced to the specimen inlet part 1 by the syringe 8. The specimen is guided to the flow channel of the glass chip through the flow channel 25 by the micropump 10, and then is brought into contact with the heater 6, where it is heated. If platinum is used for the heater which generates heat, the temperature also can be detected from the resistance value. After that, the quantity of the fluorescence emitted from the specimen is measured in a fluorescence measuring portion 7.

Figure 4A:
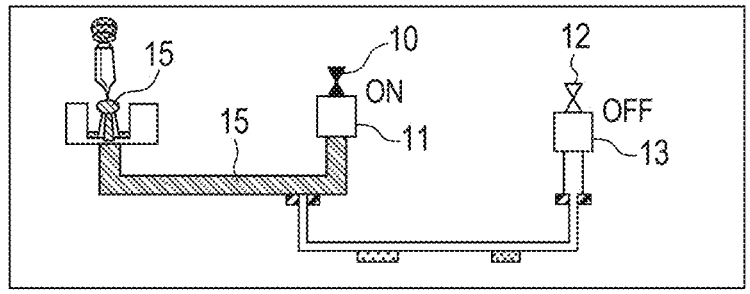
FIGS. 4A, 4B, 4C, 4D and 4E are views illustrating a method for using the device for the analysis.
Figure 4B:
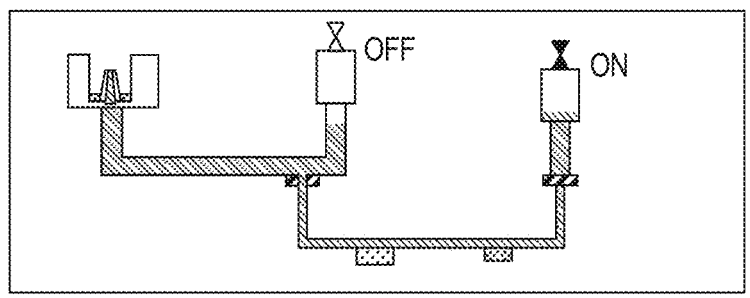
Figure 4C:
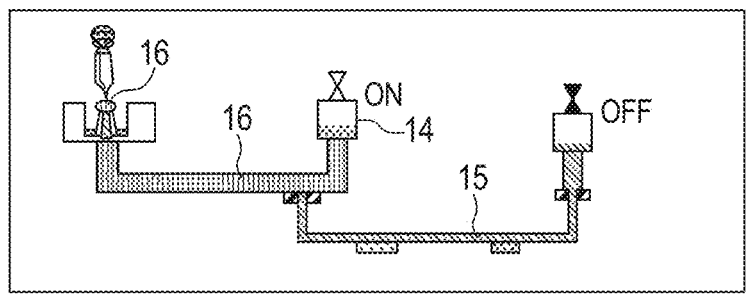
Figure 4D:
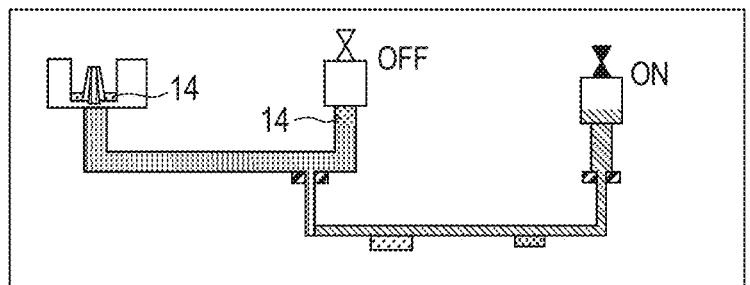
Figure 4E:
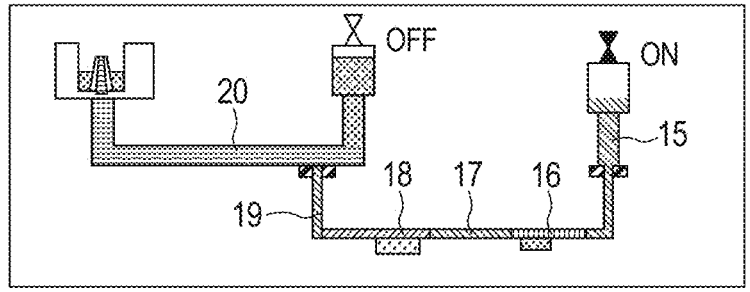

Next, the introduction of the specimen will be described with reference to FIGS. 4A to 4E. FIGS. 4A to 4E illustrate an example in which the specimen is continuously introduced into the device for analysis, which has been described in FIGS. 3A and 3B. FIG. 4A is a view illustrating the first step in which the first specimen is guided to the microfluidic device having the specimen inlet part. FIG. 4B is a view illustrating the second step in which the first specimen is guided from the microfluidic device having the specimen inlet part to the chip made from glass. FIG. 4C is a view illustrating the third step in which the second specimen is guided to the microfluidic device having the specimen inlet part. FIG. 4D is a view illustrating the fourth step in which the second specimen is guided from the microfluidic device 4 having the specimen inlet part to the chip made from glass. FIG. 4E is a view illustrating the state in which several kinds of specimens have been guided to the device for the analysis. In the figures, a waste liquid 14, the first specimen 15, the second specimen 16, the third specimen 17, the fourth specimen 18, the fifth specimen 19 and the sixth specimen 20 are shown.

The first specimen 15 is guided to the specimen inlet part in a form of a droplet by the syringe, and then is guided to fill up the flow channel 25 by a negative pressure by using a first micropump 10 or a syringe from the first specimen discharge port 11 (see FIG. 4A). Next, while the first specimen is added, in a sufficient amount to fill up the flow channel, to the specimen inlet part dropwise, the first specimen is sucked by a negative pressure from a second specimen discharge port 13 by a second micropump 12, and thereby the specimen in the flow channel 25 is guided into the flow channel 26 in the chip made from glass. Even after the flow channel 26 in the chip made from glass has been filled with the first specimen, the specimen inlet part is filled with the first specimen even to the inlet port or to the vicinity of the inlet port, due to surface tension (see FIG. 4B).

Next, the second specimen 16 is introduced to the specimen inlet part. Because the inlet channel in the specimen inlet part is filled with the first specimen, the first specimen and the introduced second specimen are integrated by the surface tension. At this time, even if air bubbles are generated, the air bubbles are exhausted from an aperture in the top face of the specimen inlet part by the surface tension. The second specimen is guided to the flow channel in the chip made from glass, in a similar way to the first specimen.

The operations are repeated, and thereby a plurality of specimens (15 to 20) in respective fixed amounts are guided to the chip made from glass (see FIG. 4E).

[Exemplary Embodiment 3]
Study on Shape of Specimen Inlet Part

Figure 5A:
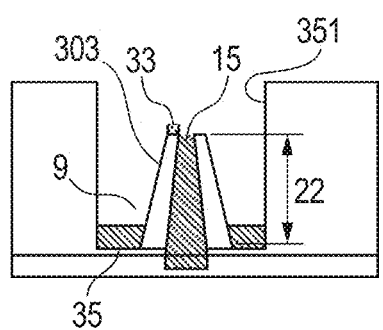
FIGS. 5A, 5B, 5C and 5D are views describing an introduction of a specimen.
Figure 5B:
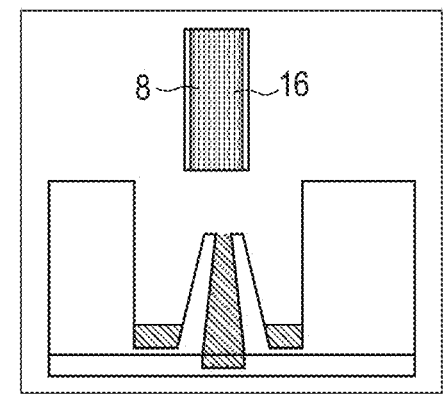

FIGS. 5A and 5B are views illustrating states of the introduction of a specimen. FIG. 5A illustrates the state in which the specimen inlet part is filled with a first specimen.

Figure 5C:
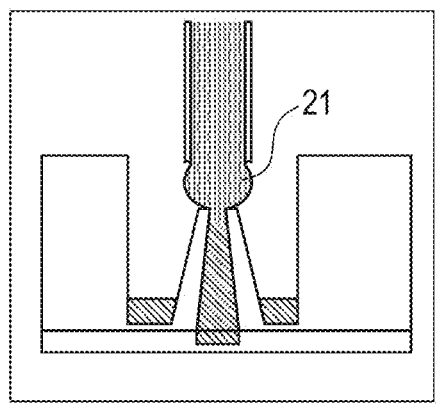
Figure 5D:
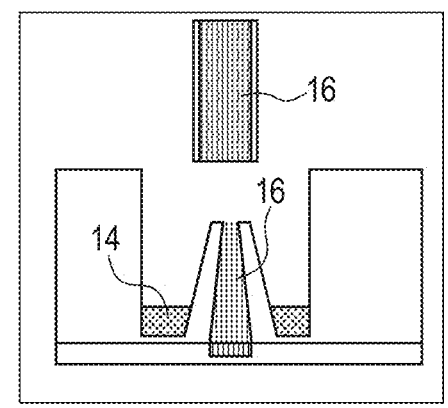

FIG. 5B illustrates the state in which the syringe that will insert the second specimen into the specimen inlet part has been arranged on an upper part of the specimen inlet part. FIG. 5C illustrates the step in which the second specimen is added to the specimen inlet part dropwise from the syringe, and is guided into the specimen inlet part. FIG. 5D illustrates the state that the specimen inlet part 1 is filled with the second specimen. In the figures, the syringe 8 for the specimen, the liquid reservoir 9, the waste liquid 14, the first specimen 15, the second specimen 16, a droplet 21, the height 22 of the specimen inlet part and the thickness 33 of the wall at the inlet port of the specimen inlet part are shown.

The specimen is sent by the pump from the specimen inlet part as in the description of FIGS. 4A to 4E, but it is difficult to strictly control the amount of the specimen. Accordingly, the specimen is excessively introduced, and a part thereof is discharged to the outer periphery of the specimen inlet part. Because of this, the specimen inlet part can have such a shape as to be capable of effectively discharging the excessive solution to the outer periphery.

Specifically, the specimen inlet part can have a shape in which a diameter of a cross section of the outer wall face continuously and gradually increases from the upper face to the bottom face, and the height 22 can be 2 mm or more.

In addition, if the thickness 33 of the wall at the inlet port becomes excessively large, the discharge efficiency is aggravated. Accordingly, the thickness of the wall at the inlet port is desirably 0.4 mm or not more than 0.4 mm.

[Exemplary Embodiment 4]
Verification on Size of Diameter of Inlet Port of Inlet Channel in Specimen Inlet Part The surface tension of the inlet channel increases as the diameter of the inlet channel increases, but a volume increases with the third power of a radius.

Accordingly, if the diameter becomes excessively large, the weight increases and it becomes difficult to keep the liquid level.

In addition, as described above, if the diameter of the inlet port is excessively large, contamination easily occurs when the specimen is introduced.

Figure 6A:
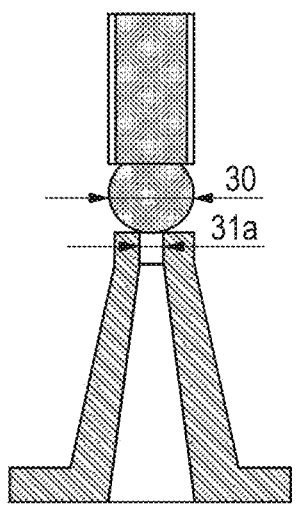
FIGS. 6A, 6B and 6C are views describing a size of the diameter of the inlet port of the flow channel in the specimen inlet part according to an embodiment of the present invention.
Figure 6B:
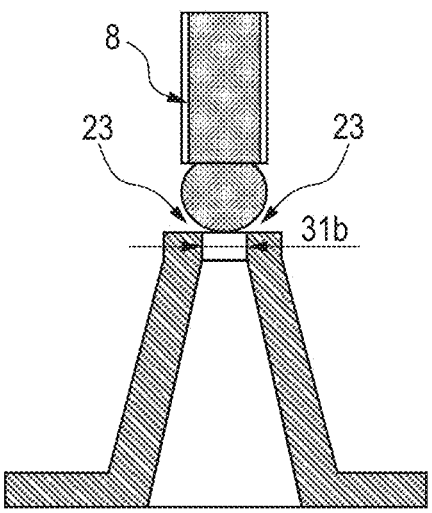
Figure 6C:
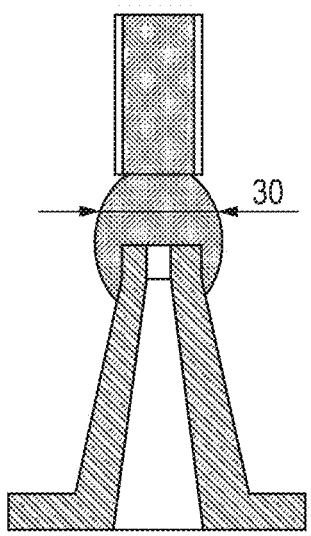

FIG. 6A is a view illustrating the specimen inlet part that has the inlet channel of which the inlet port has a suitable diameter. FIG. 6B illustrates the specimen inlet part that has the inlet channel of which the inlet port has an excessively large diameter. In addition, FIG. 6C illustrates an example of the specimen inlet part which can further reduce the contamination. In the figures, the contamination 23, a diameter 30 of a droplet, a suitable diameter 31a and an excessively large diameter 31b are shown.

The amount of the specimen which is introduced into the microfluidic device at a time is 5 μL (microliter) or not more than 5 μL. If the solution is 1 μL, the diameter is 1.24 mm, and if the solution is 5 μL, the diameter is 2.12 mm.

It has been found from an experiment that if the maximum diameter of the inlet port becomes 50% or more of the diameter of the droplet, a gap is formed between the droplet and the inlet port and the contamination 23 occurs (FIG. 6B). When the maximum diameter of the inlet port becomes 50% or more of the droplet diameter, a gap is formed due to a little deviation of the droplet from the inlet port, and the specimen inlet channel results in sucking the contamination (23) in the air. Thereby, the desired measurement results in being unable to be conducted. In consideration of the above description, the diameter of the inlet port is desirably 0.5 mm or less.

Furthermore, as illustrated in FIG. 6C, if the outer wall of the inlet port also can be wrapped by the droplet, it can be expected that the contamination is more efficiently reduced. For this purpose, the outer diameter of the inlet port is desirably 1 mm or not more than 1 mm. Specifically, it is desirable that a sum of the addition of the maximum diameter of the inlet port and the thicknesses of the wall of both sides of the inlet port is 1 mm or less.

[Exemplary Embodiment 5]
Verification that Inlet Channel having Truncated Cone Shape can keep Liquid Level The diameter of the inlet channel continuously and gradually increases as the inlet channel approaches the flow channel, or is constant in the vicinity of an inlet port and then continuously and gradually increases as the inlet channel approaches the flow channel. It was verified by simulation whether these shapes would sufficiently keep the liquid up to the inlet port.

Figure 7:
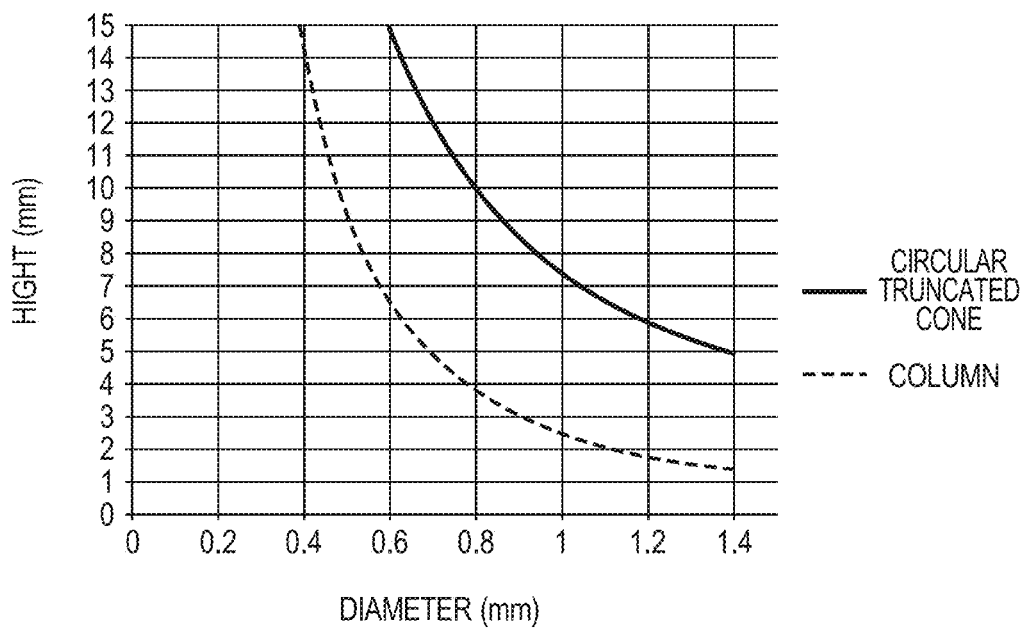
FIG. 7 is a graph illustrating a height of a liquid level which is held in the specimen inlet channel.

FIG. 7 illustrates the result obtained by the simulation that to what height the liquid level is kept from the face 50 at which the specimen comes in contact with the flow channel, on each of an inlet channel (truncated cone shape) in which the cross section of the inlet channel is a circle and the diameter thereof gradually increases as the inlet channel of the specimen inlet part approaches the flow channel, and an inlet channel (two-step columnar shape) in which the diameter of the inlet channel does not continuously and gradually increases, and which is formed of a combination of columns, when the diameters of specimen inlet ports are each 0.2 mm. Incidentally, in the simulation, the height at which the specimen is kept is determined based on the surface tension of the inlet port and a volume of the specimen in the inlet channel.

Figure 8:
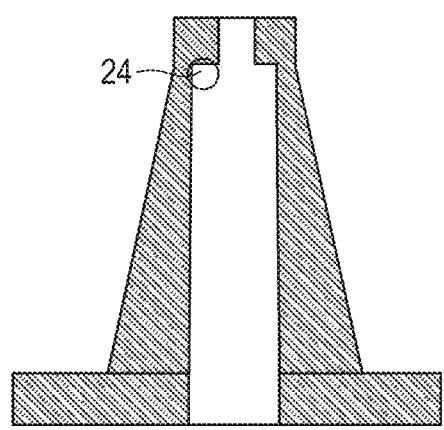
FIG. 8 is a view illustrating a dead volume in the inlet channel.

A solid line shows a result on the inlet channel having the truncated cone shape. The truncated cone has a diameter of 0.2 mm at the inlet port, and has a diameter shown on the horizontal axis of the graph, on the face at which the truncated cone comes in contact with the flow channel. A broken line shows a result on the inlet channel having the two-step columnar shape (while example of inlet channel having two-step columnar shape is illustrated in FIG. 8). The two-step column is formed of a column of the upper stage (inlet port side), which has the diameter of 0.2 mm and the height of 0.5 mm, and a column of the lower stage (flow-channel side), which has the diameter shown on the horizontal axis of the graph constantly down to the flow channel. The vertical axis of the graph shows the height of the liquid level to be kept.

As a result of the simulation, it was found that when the inlet channel having the truncated cone shape had a diameter of 1 mm on the face on which the truncated cone shape comes in contact with the flow channel, such a sufficient height of the specimen as 7 mm or higher could be obtained. When the inlet channel is a columnar shape having a diameter of 1 mm, a height of the specimen to be kept therein is 2.3 mm which is insufficient. When the inlet channel with the columnar shape intends to keep the height of 7 mm, the diameter shall be 0.5 mm. However, a columnar pin having the diameter of 0.5 mm is deformed or is broken, and accordingly it is difficult to manufacture the die.

FIG. 8 illustrates an inlet channel having the two-step columnar shape, in which the diameter of the inlet channel does not continuously and gradually increase, and which is formed of a combination of the columns or the like. Such an inlet channel is not desirable because a detention part 24 of the specimen occurs and a larger amount of the liquid is needed when the specimens are switched.

Figure 9A:
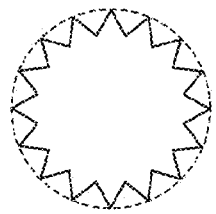
FIGS. 9A and 9B are views illustrating a shape in the vicinity of an entrance in another form of the inlet channel.
Figure 9B:
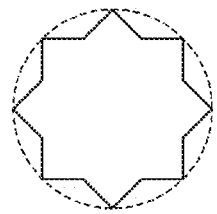

[Exemplary Embodiment 6]
Verification of the Shape of the Cross Section of Inlet Channel FIGS. 9A and 9B are views illustrating shapes of the cross section of the inlet channel. The cross section of the inlet channel does not necessarily need to be a circle, but may be an elliptical shape, a polygonal shape or another shape. FIG. 9A illustrates a cross section having a petal shape. FIG. 9B illustrates a cross section having another petal shape.

The inlet channel having the petal shape has a longer outer periphery than that of a circle, though the petal shape has the same diameter as that of the circle, and accordingly is more advantageous in a point that the surface tension is increased.

[Exemplary Embodiment 7]
Inlet Part provided with Bump

Figure 10A:
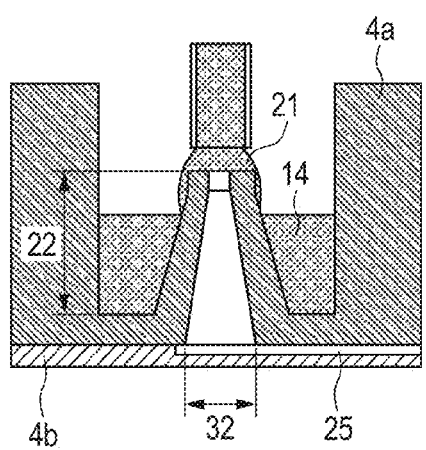
FIGS. 10A and 10B are views describing a mixture of a droplet and a waste liquid.
Figure 10B:
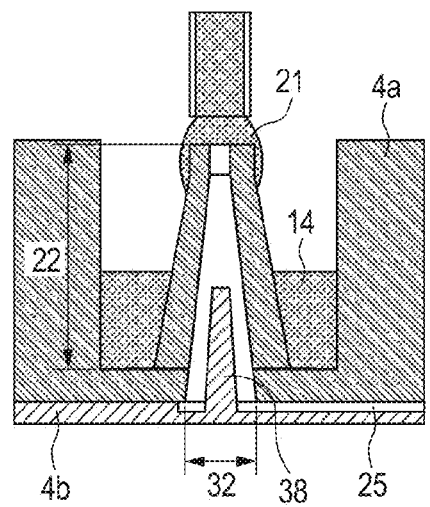

FIGS. 10A and 10B are views describing a mixture of a droplet and a waste liquid. FIG. 10A illustrates a configuration where the droplet and the waste liquid mix with each other. FIG. 10B illustrates a configuration where the droplet and the waste liquid does not mix with each other. A bump 38 is shown in the figure.

When a plurality of specimens are introduced repeatedly, the waste liquid 14 gradually increases on the outer periphery of the inlet part. Accordingly, when the specimen is introduced many times, the droplet 21 and the waste liquid 14 occasionally mix with each other, and in order to prevent the mixture, it is occasionally necessary to increase the height 22 of the specimen inlet part. FIG. 10A illustrates a state in which the droplet 21 and the waste liquid 14 mixes with each other as a result of repeatedly carried out introductions of the specimens because the height 22 of the specimen inlet part is low. As a result, the desired measurement is unable to be conducted any more.

However, if the height 22 of the specimen inlet part is simply increased, the volume of the specimen in the inlet channel increases by the volume corresponding to the difference, and the weight of the specimen increases. Accordingly, the height of the specimen cannot be kept by the surface tension of an inlet port of the inlet channel, and air bubbles result in being mixed. Then, it is conceivable to decrease the diameter 32 of the inlet channel in the face which comes in contact with the flow channel, for reducing the volume of the inlet channel. However, in this case, the pin in the inner part of the die for forming the inlet channel becomes thinner and become becomes difficult to be molded with a die because the pin may be broken or deformed.

When a plurality of specimens are introduced repeatedly, the waste liquid 14 gradually increases on the outer periphery of the inlet part. Accordingly, when the specimen is introduced many times, the droplet 21 and the waste liquid 14 occasionally mixes with each other, and in order to prevent the mixture, it is occasionally necessary to increase the height 22 of the specimen inlet part. FIG. 10A illustrates a state in which the droplet 21 and the waste liquid 14 mixes with each other as a result of repeatedly carried out introductions of the specimens because the height 22 of the specimen inlet part is low, and desired measurement results in being unable to be conducted any more.

However, if the height 22 of the specimen inlet part is simply increased, the volume of the specimen in the inlet channel increases by the volume corresponding to the difference, and the weight of the specimen increases. Accordingly, the height of the specimen cannot be kept by the surface tension of an inlet port of the inlet channel, and the air bubbles result in being mixed. Then, it is conceivable to decrease the diameter 32 of the inlet channel in the face which comes in contact with the flow channel, for reducing the volume of the inlet channel. However, in this case, the pin in the inner part of the die for forming the inlet channel becomes thinner, and accordingly the pin is broken or is deformed to become difficult to be molded with a die.

In order to solve the above described problem, the specimen inlet channel is effective which has the bump in the inner part, as illustrated in FIG. 10B. In addition, such a method can be employed as to provide the bump 38 on a component 4b which forms the flow-channel shape and bond the component 4b with a component 4a that has the specimen inlet part formed therein and forms the hole shape. By having the bump provided therein, the microfluidic device can reduce the volume of the inner part of the inlet channel without decreasing the diameter 32 of the inlet channel in the face which comes in contact with the flow channel, and accordingly can increase the height 22 of the specimen inlet part while keeping such a shape as to be capable of being molded with a die. In the shape in FIG. 10B, the height 22 of the specimen inlet part is sufficiently high, and accordingly it can be suppressed that the droplet and the waste liquid 14 mixes with each other.

The bump 38 illustrated in FIG. 10B shows a truncated cone shape for the sake of convenience, but may have another shape. For instance, even though the bump has a conical shape, a polygonal pyramid shape, a polygonal truncated pyramid shape or the like, the same effect can be obtained. However, a columnar shape and a polygonal column shape which are unsuitable for the molding and are not employed. In addition, the bump does not necessarily exist in the middle of the inlet channel.

[Exemplary Embodiment 8]

In the microfluidic device of the present invention, the specimen is held at a constant height at the specimen inlet port by the surface tension of the specimen. As a result, the microfluidic device prevents air bubbles from mixing with the specimen, when the specimens are continuously introduced thereinto. The microfluidic device of the present invention is manufactured with the molding, and accordingly the cost of the manufacture is reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2012-179384, filed on Aug. 13, 2012 and No. 2013-160964, filed on Aug. 2, 2013, which are hereby incorporated by reference herein in its entirety.

What is claimed is:

1. A microfluidic device comprising:
a first component including a bump; and
a second component including a specimen inlet part, the specimen inlet part having:
an inlet port; and
an inlet channel for introducing a specimen into a flow channel, wherein the inlet channel has one of (i) a diameter which continuously and gradually increases as the inlet channel approaches the flow channel, and (ii) a diameter which is constant in the vicinity of the inlet port and then continuously and gradually increases as the inlet channel approaches the flow channel, and
wherein the first component and the second component are bonded so that the specimen inlet part forms a hole shape fluidly connected to the flow channel and the bump is disposed inside of the hole shape to reduce a volume of the hole shape without decreasing the diameter of the inlet channel, such that a void surrounds the sides and the to of the bump such that the specimen is configured to flow around the bump.

2. The microfluidic device according to claim 1, wherein the inlet channel has a diameter less than or equal to 0.5 mm at the inlet port.

3. The microfluidic device according to claim 1, wherein the specimen inlet part has an outer diameter which continuously and gradually increases from an upper face of the specimen inlet part to a bottom face of the specimen inlet part.

4. The microfluidic device according to claim 1, wherein the specimen inlet part has an outer wall with a thickness less than or equal to 0.4 mm at the inlet port.

5. The microfluidic device according to claim 1, wherein the specimen inlet part has a height greater than or equal to 2 mm.

6. The microfluidic device according to claim 1, wherein the flow channel leads to a micro flow channel.

7. The microfluidic device according to claim 6, further comprising a pump configured (i) to introduce a first specimen to the inlet channel, to the flow channel, and to the micro flow channel, and (ii) to introduce a second specimen to the inlet channel, to the flow channel and to the micro flow channel.

8. The microfluidic device according to claim 1, wherein the specimen inlet part has a liquid reservoir in the outer periphery thereof.

9. A microfluidic device comprising:
a specimen inlet part;
a bump; and
a flow channel,
wherein the specimen inlet part forms a hole shape fluidly connected to the flow channel and the bump is disposed inside of the hole shape to reduce a volume of the hole shape without decreasing the diameter of the inlet channel, such that a void surrounds the sides and the top of the bump such that the specimen is configured to flow around the bump.

* * * * *